US009441021B2

(12) United States Patent
Suck et al.

(10) Patent No.: US 9,441,021 B2
(45) **Date of Patent: *Sep. 13, 2016**

(54) PROCESS FOR THE PREPARATION OF HYPOALLERGENIC MAJOR BIRCH POLLEN ALLERGEN RBET V 1

(75) Inventors: Roland Suck, Hamburg (DE); Helmut Fiebig, Schwarzenbek (DE); Oliver Cromwell, Wentorf (DE)

(73) Assignee: MERCK PATENT GMBH, Darmstadt (DE)

( * ) Notice: Subject to any disclaimer, the term of this patent is extended or adjusted under 35 U.S.C. 154(b) by 276 days.

This patent is subject to a terminal disclaimer.

(21) Appl. No.: 12/167,712

(22) Filed: Jul. 3, 2008

(65) Prior Publication Data

US 2009/0069236 A1 Mar. 12, 2009

Related U.S. Application Data

(62) Division of application No. 10/505,897, filed as application No. PCT/EP03/01246 on Feb. 7, 2003, now abandoned.

(30) Foreign Application Priority Data

Feb. 27, 2002 (EP) .................................... 02004567

(51) Int. Cl.

| | |
|---|---|
| ***C12P 21/06*** | (2006.01) |
| ***C07K 1/00*** | (2006.01) |
| ***C07K 14/00*** | (2006.01) |
| ***C07K 16/00*** | (2006.01) |
| ***C07K 17/00*** | (2006.01) |
| ***C07K 14/415*** | (2006.01) |
| *A61K 38/00* | (2006.01) |
| *A61K 39/00* | (2006.01) |

(52) U.S. Cl.

CPC ............. *C07K 14/415* (2013.01); *A61K 38/00* (2013.01); *A61K 39/00* (2013.01)

(58) Field of Classification Search

None

See application file for complete search history.

(56) References Cited

U.S. PATENT DOCUMENTS 6,900,034 B2 * 5/2005 Suck et al. ................... 435/69.1

FOREIGN PATENT DOCUMENTS

WO WO 0220559 3/2002

OTHER PUBLICATIONS

Mukhopadhyay et al. 'Inclusion bodies and purfication of proteins in biologically active forms.' Adv. Biochem. Eng. 56:61-109, 1997.*

Cromwell et al. 'Transition of recombinant allergens from bench to clinical application.' Methods 32:300-312, 2004.*

Hoffmann-Sommergruber Karin et al.: "High-Level Expression and Purification of the Major Birch Pollen Allergen, BET V 1." Protein Expression and Purification, vol. 9, No. 1, 1997, pp. 33-39.

Vrtaia et al. 'Humoral immune responses to recombinant tree pollen allergens (Bet v i and Bet v II) in mice : construction of a live oral allergy vaccine.' Int. Arch Allergy Immunol. 107(1-3):290-294, 1995.

Hoffmann-Sommergruber et al. "High-level expression and purification of the major birch pollen allergen, Bet v 1." Protein Expr Purif. Feb. 1997;9(1):33-9.

Breiteneder et al. "The gene coding for the major birch pollen allergen Betv1 , is highly homologous to a pea disease resistance response gene." EMBO J. Jul. 1989; 8(7): 1935-1938.

Kahlert et al. "Characterization of a hypoallergenic recombinant Bet v 1 variant as a candidate for allergen-specific immunotherapy." Int Arch Allergy Immunol. 2008;145(3):193-206.

* cited by examiner

*Primary Examiner* — Nora Rooney

(74) *Attorney, Agent, or Firm* — Millen, White, Zelano, Branigan, P.C.

(57) ABSTRACT

The invention relates to a process for the preparation of hypoallergenic major birch pollen allergens by means of one or more chromatographic purification steps using essentially unbuffered aqueous bases as eluent and subsequent neutralization. The hypoallergenic major birch pollen allergens are distinguished by a lack of, but at least by reduced immunoglobulin E binding with simultaneous retention of therapeutically relevant T-cell stimulation. They can therefore be employed as low-side-effect therapeutic agents for specific immunotherapy.

4 Claims, 5 Drawing Sheets

Fig. 4

Figure 1A:
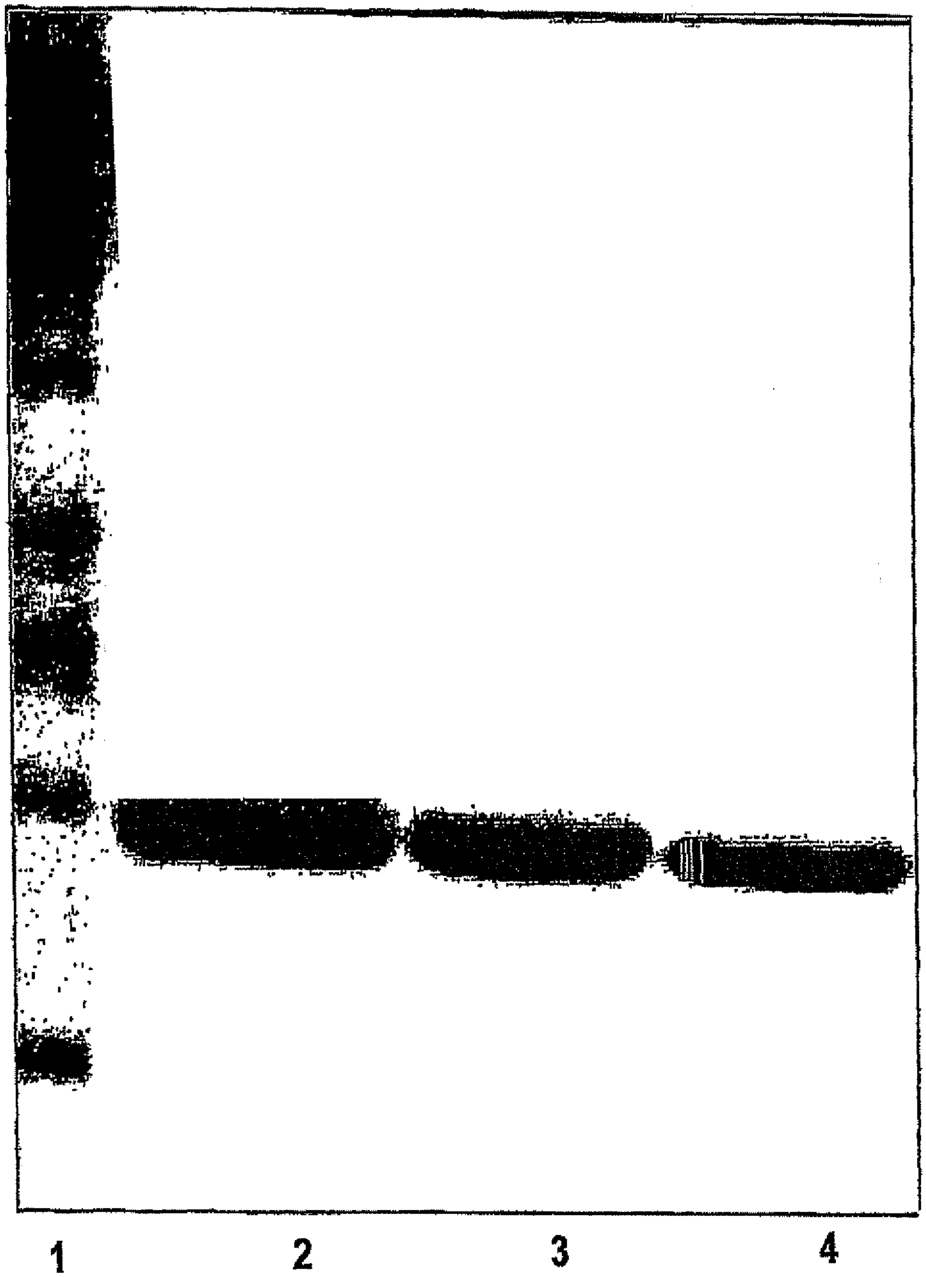

| Proliferation [SI] | | | | | | | |
|---|---|---|---|---|---|---|---|
| Protein Concentration [µmol/l] | | TCL 65.15 | 36.15 | 52.12 | 68.19 | TCC 51.25A9 | 3.6E6 |
| nBet v1 | 0,3 | 23,6 | 30,8 | 13,7 | 3,2 | 9,2 | 3,5 |
| rBet v1 | 0,3 | 21,5 | 18,7 | 7,8 | 5,4 | 5,8 | 3,2 |
| rBet v1-MF | 0,3 | 28,2 | 42,5 | 16,4 | 7,2 | 10,2 | 4,1 |

PROCESS FOR THE PREPARATION OF HYPOALLERGENIC MAJOR BIRCH POLLEN ALLERGEN RBET V 1

This application is a divisional of U.S. patent application Ser. No. 10/505,897, filed Aug. 27, 2004, which was the National Stage application under §371 of PCT/EP03/01246, filed Feb. 7, 2003, all of which is incorporated by reference herein.

TECHNICAL AREA OF THE INVENTION

The invention relates to a process for the preparation of birch pollen allergens which are distinguished by a lack of, but at least by reduced immunoglobulin E binding, i.e. by hypoallergeneity. These allergens completely retain therapeutically relevant T-cell stimulation. They can therefore be employed as low-side-effect therapeutic agents for specific immunotherapy.

BACKGROUND OF THE INVENTION

Type 1 allergies have dramatically increased worldwide in recent decades. Up to 20% of the population in industrialised countries suffer from complaints, such as allergic rhinitis, conjunctivitis or bronchial asthma, which are caused by allergens present in the air (aeroallergens), which are released by various sources, such as plant pollen, mites, mammals (cats, dogs, horses) and mould fungi. Severe allergies can also be initiated by insect stings or bites, such as, for example, of bees and wasps.

The type 1 allergy-initiating substances are proteins, glycoproteins or polypeptides. These allergens react via the mucous membranes after ingestion or with the IgE antibodies bound to the surface of mast cells in sensitised people after stings or bites. If two or more IgE antibodies are crosslinked to one another by an allergen, this results in the release of mediators (for example histamine, prostaglandins) and cytokines by the effector cell and thus in initiation of the allergic symptoms.

Birch pollen are the most frequent initiators of allergic reactions amongst tree pollen (Jarolim E. et al., 1989, Allergy 44:385-95). More than 90% of sufferers from birch pollen allergies have IgE antibodies against the major allergen Bet v 1 (Elfman, L. et al., 1997, Int. Arch. Allergy Immunol., 113: 249-51).

With the aid of cDNA sequences, it is possible to prepare recombinant allergens which can be used in the diagnostics and therapy of allergies. (Scheiner and Kraft, 1995, Allergy 50, 384-391). The preparation of recombinant Bet v 1 allergens (rBet v 1) and their purification for pharmaceutical purposes has been described, for example, by Hoffmann-Sommergruber et al. (Protein Exp. Purif. 9 (1), 1997: 33-39).

In addition, specific genetic modification of recombinant allergens is possible, enabling a reduced allergenic potential to be achieved (Schramm et al. 1999, J. Immunol. 162 (4); 2406-2414; Valenta et al., 1999, Biol. Chem. 380: 815-24; Singh et al., 1999, Int. Arch. Allergy Immunol. 119: 75-85). Allergen variants of this type are promising future candidates for specific immunotherapy of type 1 allergy.

However, a potential disadvantage in recombinant allergen variants is that the modification of the primary structure causes loss or a reduction in the reactivity of the T-cell epitopes which are necessary for therapeutic success. This possibility can only be excluded if the primary structure corresponding to the natural allergen serves as the basis for the preparation of the recombinant protein.

In the case of major birch pollen allergen Bet v 1, the preparation was carried out in two halves (Vrtala, S., et al., 1997, J. Clin. Invest. 99: 1673-81) or as a trimer (Vrtala, S., et al., 1999, Int. Arch. Allergy Immunol. 118:218-9) in order to optimise it for therapeutic purposes, i.e. to reduce the IgE binding capacity, by recombinant methods. The potential loss of T-cell epitopes and the insolubility of the proteins also has a disadvantageous effect in these approaches. A further disadvantage here can be seen in the complex manner of preparation of these rBet v 1 variants.

A suitable starting point for the preparation of a recombinant major allergen rBet v 1 which can be utilised for therapeutic purposes would accordingly be a molecule which corresponds to the wild type in the primary structure and is unrestricted in its T-cell stimulation, but has reduced IgE activity, i.e. is hypoallergenic.

This object has been achieved in accordance with the present invention by the performance of a series of biochemical purification steps known per se using soluble recombinant major allergen rBet v 1 as starting material, Surprisingly, a reduced IgE activity and at the same time maintained T-cell stimulation has been observed in the proteins purified in this way. Accordingly, the process according to the invention provides improved therapeutic efficacy at the same time as a significant reduction in or absence of side effects.

The form of the preparation process of the recombinant allergens is of particular importance here inasmuch as the proteins are converted in the course of this process into a conformation which has no or greatly reduced affinity to IgE with constant T-cell stimulation.

FIGURES

FIG. 1A: SDS-PAGE for characterisation of hypoallergenic rBet v 1

Track 1: Protein standard for estimation of the molecular weight

Track 2: Natural rBet v 1

Track 3: rBet v 1 purified in accordance with the invention

Track 4: Conventionally purified rBet v 1

Figure 1B:
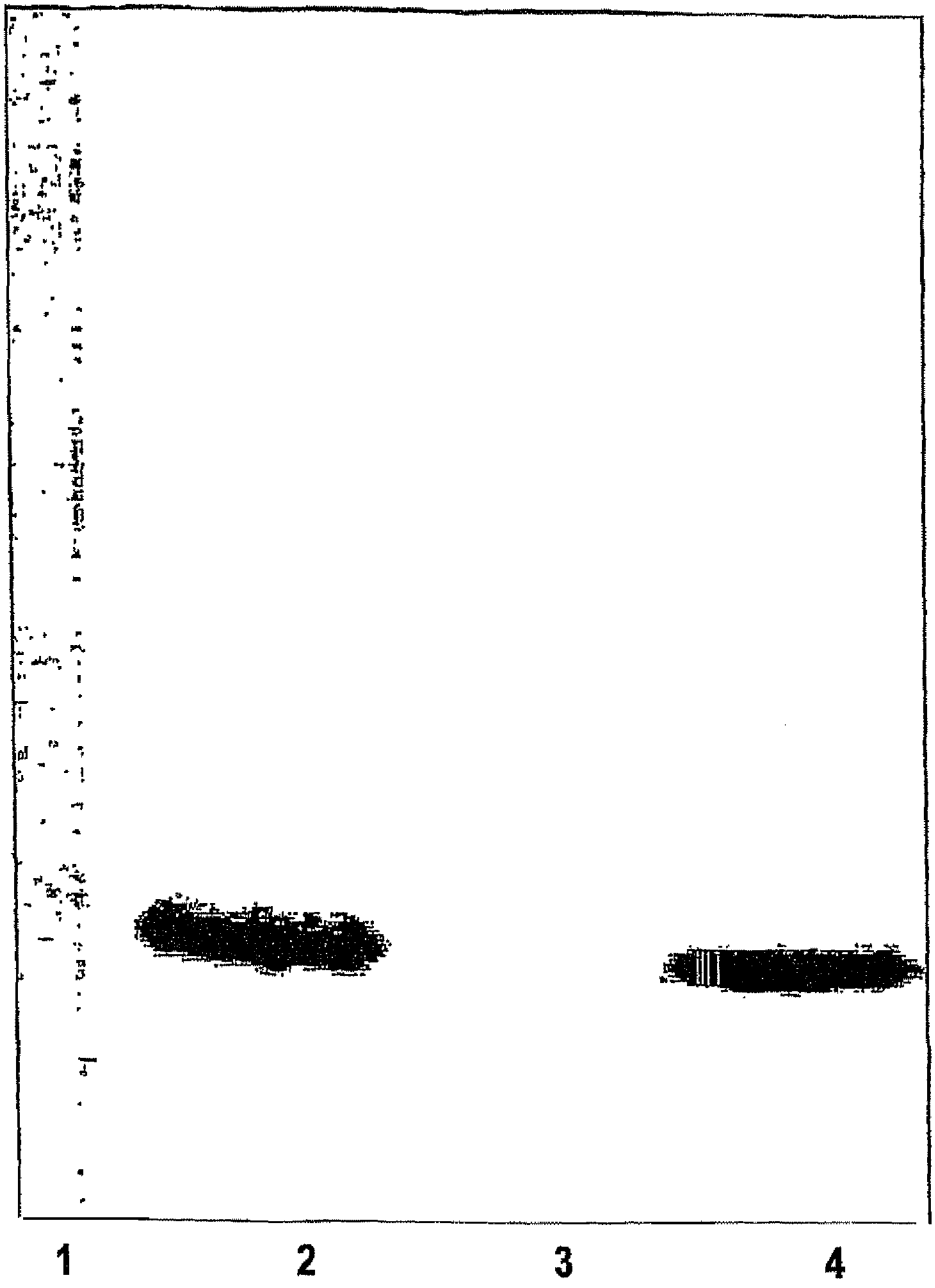

FIG. 1B: Nitrocellulose blot of the SDS-PAGE from FIG. 1A

Figure 2B:
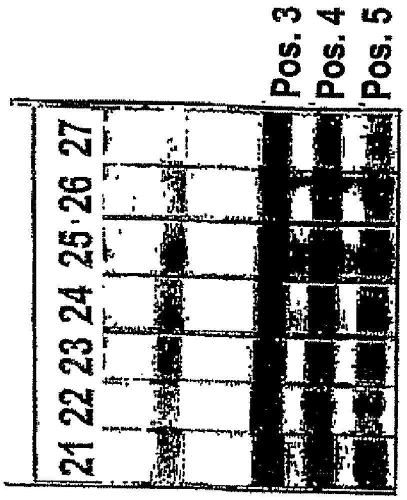
Figure 2A:
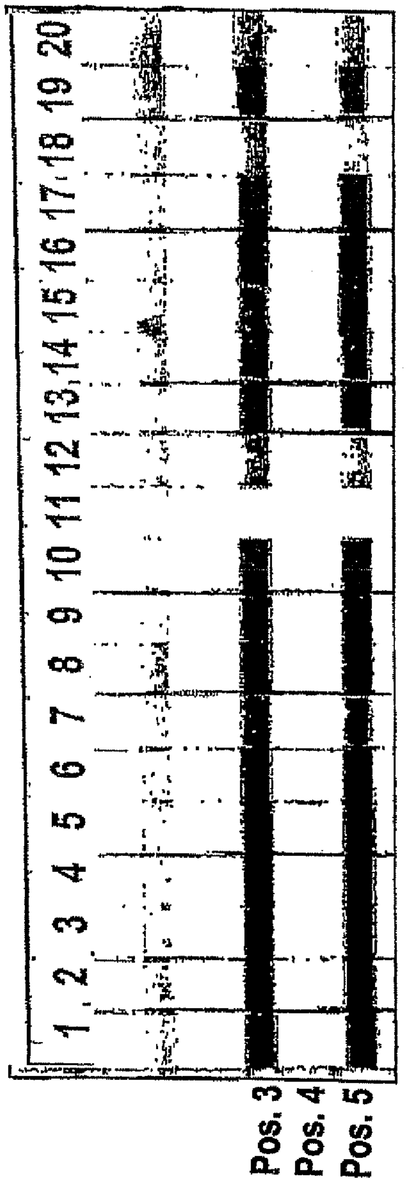

FIG. 2A: Nitrocellulose blot for determination of the IgE activity with 20 individual patient sera Position 3: Natural rBet v 1

Position 4: rBet v 1 purified in accordance with the invention

Position 5: Conventionally purified rBet v 1

FIG. 2B: Nitrocellulose blot for determination of the identity of Bet v 1 samples Blots 21-26: Various polyclonal rabbit anti-Bet v 1 antibodies Blot 27: Monoclonal mouse anti-Bet v 1 antibody 6B6

Figure 3:
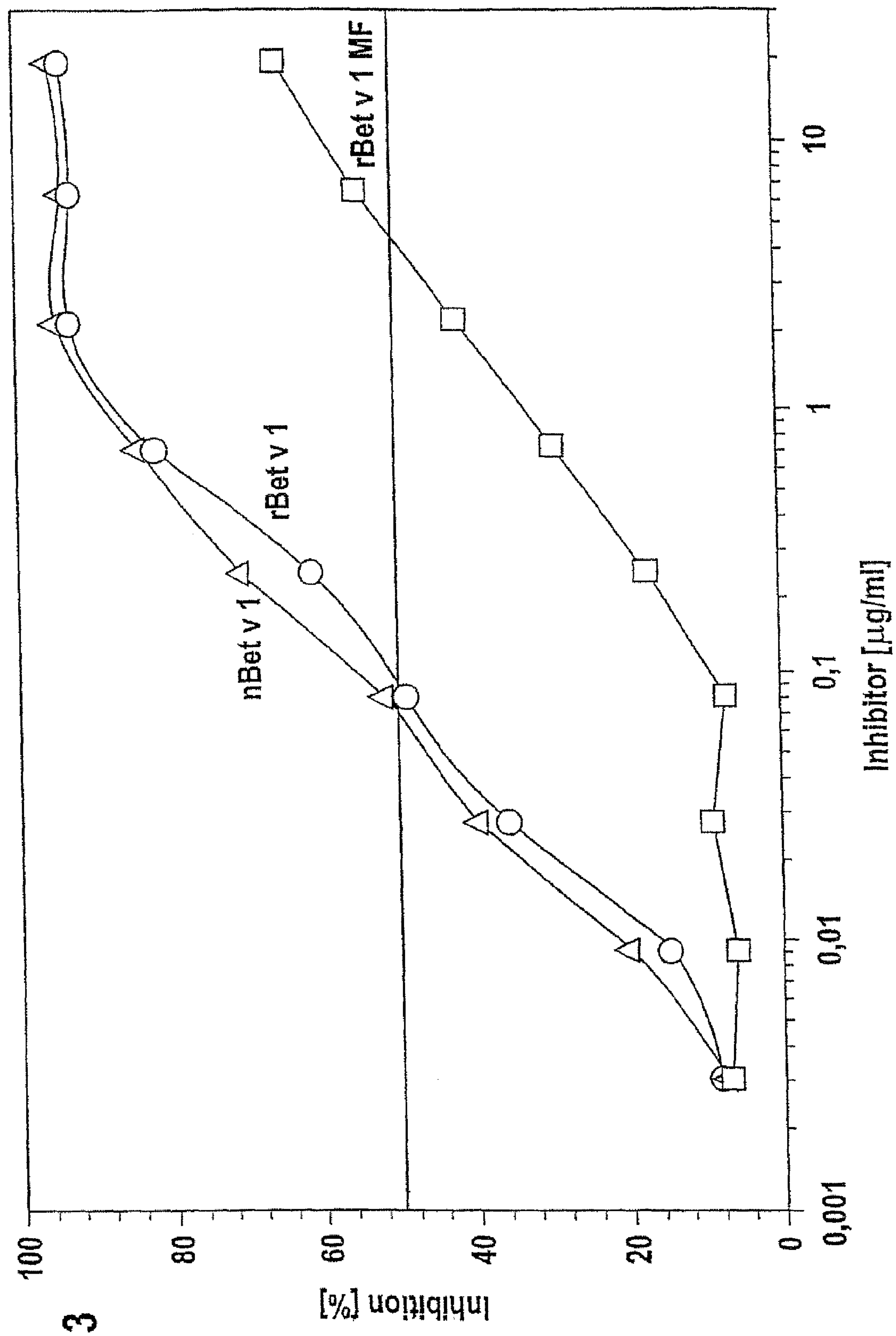

FIG. 3: Enzyme allergo sorbent test (EAST) for quantification of IgE binding The concentration of an inhibitor of IgE-Bet v 1 binding in μg/ml is plotted on the vertical axis, and the degree of inhibition in [%] is shown on the horizontal axis.

FIG. 4: Determination of T-cell stimulation by Bet v 1 variants

The concentrations of natural rBet v 1, of conventionally purified recombinant rBet v 1 and of recombinant rBet v 1 purified in accordance with the invention and the respective stimulation indices (SI) obtained with various T-cell lines (TCLs) and T-cell clones (TCCs) are compared.

DETAILED DESCRIPTION OF THE INVENTION

The present invention relates to a biochemical purification process which results in the preparation of proteins having the properties modified in accordance with the invention via efficient purification, using specific eluents, of, for example, allergens prepared by recombinant methods. These properties consist in a lack of, but at least a greatly reduced IgE activity, with simultaneous maintenance of T-cell stimulation.

The invention thus relates to a process for reducing the IgE activity of the major birch pollen allergen rBet v 1 which consists in the use of soluble recombinant major birch pollen allergen rBet v 1 and in carrying out the chromatography steps described below for the purification thereof and the subsequent neutralisation step.

The invention furthermore relates to a process for the preparation of hypoallergenic major birch pollen allergen rBet v 1 by means of a plurality of chromatographic purification steps using essentially unbuffered aqueous bases as eluent and subsequent neutratisation, where the starting material employed is a soluble rBet v 1 crude protein prepared by recombinant methods.

The chromatographic purification steps preferably include anion exchange chromatography, hydrophobic interaction chromatography and gel filtration and can be carried out once, a number of times one after the other or a number of times alternately. However, the chromatographic purification steps are preferably carried out in the following sequence: first gel filtration, anion exchange chromatography, hydrophobic interaction chromatography, second get filtration.

The chromatographic purification is usually carried out with a base concentration of from 5 to 100 mM, but preferably with from 5 to 40 mM and particularly preferably with from 10 to 30 mM, where the basic substance employed is preferably NaOH. Instead of a purely aqueous system, it is also possible to use a mixed system comprising, for example, water and methanol. A non-aqueous, for example methanol system is also conceivable. However, preference is given to the use of an aqueous system.

Depending on the respective chromatography step, different concentrations of a neutral salt—preferably NaCl—up to about 5 M can be added to the eluent.

Any reduction in the pH that may be necessary to values which are tolerated by relatively sensitive proteins can be achieved by the addition of sodium hydrogencarbonate.

The intention of establishing physiological conditions at the end of the purification can also be a reason for the presence of sodium hydrogencarbonate during the chromatography steps. Concentrations of up to 100 mM are basically possible here. However, work is preferably carried out in the physiological range below 20 mM, particularly preferably at 11 mM.

In the case of rBet v 1, a reduction in the pH is not necessary. Nevertheless, sodium hydrogencarbonate is generally added on application of the process according to the invention to rBet v 1 in order to be able to establish physiological concentrations in a simple manner at the end of the purification.

The invention thus relates to a process for the preparation of hypoallergenic major birch pollen allergen rBet v 1 in which essentially unbuffered basic eluents maintain the proteins to be purified in solution under mild conditions and thus in a chromatographable state.

In a preferred embodiment of the process, the rBet v 1 crude protein is pre-purified before the actual purification by chromatography, for example hydrophobic interaction chromatography or ion exchange chromatography, and/or salt precipitation, where, in contrast to the subsequent principal purification, a buffered eluent or a buffered solution is used.

The starting materials for the process are soluble, recombinant allergens expressed in bacteria or other suitable host cells (such as, for example, yeasts). Since the process represents a general application for these expression products, soluble allergens of different origin can also, in accordance with the invention, be purified by the process, renatured and formulated. In particular in the case of corresponding similarity of these allergens of different origin to the major birch pollen allergen Bet v 1, it can be expected that the properties according to the invention will be achieved. However, the process is particularly suitable for obtaining major birch pollen allergen rBet v 1 prepared by recombinant methods. However, natural major birch pollen allergen rBet v 1 is also basically suitable as starting material.

Final neutralisation of the recombinant active ingredients by modifying the pH enables—given a corresponding choice of concentration of the eluent ingredients—a ready-to-use physiological solution to be obtained directly.

The pharmaceutical active ingredients can be used directly after neutralisation as parenteral products. In addition, the reproducible and standardisable process can be carried out under the conditions of Good Manufacturing Practice (GMP), which is necessary for pharmaceuticals.

The invention thus serves for the preparation of improved preparations for the specific immunotherapy of allergies, which is achieved by the process according to the invention. The greatly reduced or lack of IgE activity provides advantageous properties for specific immunotherapy. Recombinant hypoallergenic allergens prepared in this way can thus contribute to improved therapy of allergic diseases.

The invention therefore relates to a hypoallergenic major birch pollen allergen rBet v 1 obtainable by the process according to the invention, in particular in its use as medicament.

It is of course possible, for additional influencing of the properties of major birch pollen allergen rBet v 1—for example in order to achieve a further reduction in the IgE activity or a further increase in T-cell stimulation—to make pharmaceutically acceptable modifications to the protein and thus to produce derivatives of the protein. These modifications can on the one hand be genetic modifications at the DNA level, where, for example, amino acid insertions, deletions and replacements, cleavage of the protein into fragments and fusion of the protein or fragments thereof with other proteins or peptides are suitable. However, the modifications can also be of a chemical nature and take place at the protein level.

The invention thus relates to the use of hypoallergenic major birch pollen allergen rBet v 1 according to the invention and/or pharmaceutically usable derivatives thereof, including mixtures thereof in all ratios, for the preparation of a medicament for the specific immunotherapy of allergies in the initiation of which major birch pollen allergen Bet v 1 is involved. Finally, the invention relates to a pharmaceutical composition comprising hypoallergenic major birch pollen allergen rBet v 1 according to the invention and/or pharmaceutically usable derivatives thereof, including mixtures thereof in all ratios. The active ingredients according to the invention can be converted here into a suitable dosage form together with at least one solid, liquid and/or semi-liquid excipient or adjuvant and optionally in combination with one or more further active ingredients.

These compositions can be used as therapeutic agents in human or veterinary medicine. Suitable excipients are organic or inorganic substances which are suitable for parenteral administration and do not react with hypoallergenic major birch pollen allergen rBet v 1. Suitable for parenteral administration are, in particular, solutions, preferably oil-based or aqueous solutions, furthermore suspensions, emulsions or implants. Hypoallergenic major birch pollen allergen rBet v 1 according to the invention can also be lyophilised and the resultant lyophilisates used, for example, for the preparation of injection preparations. The compositions indicated can be sterilised and/or comprise adjuvants, such as lubricants, preservatives, stabilisers and/or wetting agents, emulsifiers, salts for modifying the osmotic pressure, buffer substances and/or a plurality of further active ingredients.

Furthermore, corresponding formulation of hypoallergenic major birch pollen allergen rBet v 1 according to the invention enables depot preparations to be obtained, for example through adsorption onto aluminium hydroxide.

The preparation process according to the invention is described in general form below. In this description, all chromatography materials mentioned by way of example come from Amersham Biosciences (Freiburg, Germany). A first pre-purification step for removal of nucleic acids can consist of hydrophobic interaction chromatography carried out under physiological conditions (at a pH of 6-8, non-denaturing), where the target protein is simultaneously focused. Alternatively, salt precipitation or ion exchange chromatography can also be carried out. However, it is not absolutely necessary to carry out this first pre-purification step for achieving the effect according to the invention.

The next purification step serves to convert the proteins into weakly saline eluent in the concentration range 10-100 mM, for example 20 mM NaCl, for example by means of gel filtration on a Sephadex G-25 column. Conditions are thus created which facilitate the performance of ion exchange chromatography using alkaline eluents. The protein solution prepared in this way is subsequently employed for anion exchange chromatography, for example using a Source Q column. Most allergens are bound to the support here. The alkaline eluent causes even previously sparingly soluble or insoluble proteins to remain in solution. NaCl gradient elution results in partial removal of bacterial impurities and active-ingredient fragments.

In two further purification steps, hydrophobic interaction chromatography and gel filtration, the pre-purified and equilibrated allergens are essentially separated from bacterial impurities still remaining. To this end, use is basically made of the same eluent substances consisting of low-molar base and a varying proportion of an inorganic neutral salt. Thus, the allergens can be bound to the column in hydrophobic interaction chromatography using, for example, up to 5 M NaCl, 20 mM NaOH and 11 mM $NaHCO_3$ and subsequently eluted using low-salt or salt-free alkaline solution, for example 20 mM NaOH.

In the final chromatography step, an eluent change is carried out in such a way that the purified recombinant proteins are obtained in soluble, ready-to-use form by simple neutralisation of the base present in the eluent using a corresponding acid. Given a suitable choice of the concentrations of the eluent additives, a physiological solution which is suitable for parenteral products is formed.

The purified allergens are identified via their known physical, chemical or biological properties, in particular by means of SDS-PAGE and specific monoclonal antibodies. For further characterisation, an EAST inhibition assay (EAST denotes enzyme allergo sorbent test), with which the specific IgE binding of a protein compared to a reference cane be determined, and/or a T-cell proliferation assay, for example, can be carried out. The solvent is tested by pH measurement and quantification of the $Na^+$ and $Cl^-$ and, if desired, $CO_3^{2-}$ concentration. These methods are generally known and described.

The yield of the allergens prepared in accordance with the invention is generally 75-95%, based on the starting protein.

The process thus involves minimal sample treatments, short sample standing times, preferably the use of exclusively pharmacologically compatible substances, compatibility of a single eluent with diverse separation principles, and the avoidance of lengthy and under certain circumstances non-validatable methods, such as dialysis, in addition, the sodium hydroxide solution preferably employed as base, which is known as an effective bacteriostatic, prevents the proteins present therein from being degraded or contaminated by microorganisms. Endotoxins, which can cause problems in bacterial expressions, other foreign proteins and DNA are likewise effectively removed or degraded.

The sequence and number of chromatography steps described above can be changed. Thus, inter alia, the specific physicochemical properties of the target proteins can be taken into account.

Even without further comments, it is assumed that a person skilled in the art will be able to utilise the above description in its broadest scope. The preferred embodiments described below should therefore merely be regarded as descriptive disclosure which is absolutely not limiting in any way.

A particularly preferred embodiment of the process is shown in the following scheme (Tab. 1):

TABLE 1

| Overview of the preparation process according to the invention |
|---|
| 1. Pre-purification (optional) hydrophobic interaction chromatography (phenyl-Sepharose)<br>Eluent 1: 20 mM Tris/HCl, 1 M ammonium sulfate, pH 8.0<br>Eluent 2: dist. water |
| 2. Eluent change for the main purification gel filtration (Sephadex 25)<br>Eluent 20 mM NaCl |
| 3. Anion exchange chromatography (Source 15Q)<br>Eluent 1: 20 mM NaOH, 11 mM $NaHCO_3$ and 20 mM NaCl<br>Eluent 2: NaCl gradient (from 20 mM NaOH; 11 mM $NaHCO_3$; 20 mM NaCl to 20 mM NaOH; 11 mM $NaHCO_3$; 0.5 M NaCl) |
| 4. Hydrophobic interaction chromatography (Source PHE)<br>Eluent 1: 3 M NaCl, 20 mM NaOH, 11 mM $NaHCO_3$<br>Eluent 2: 20 mM NaOH |
| 5. Gel filtration (Superdex 75)<br>Eluent: 10 mM NaOH, 11 mM $NaHCO_3$ and 148.4 mM NaCl |
| 6. Neutralisation using 1/10 (v/v) 100 mM HCl |

The invention is described below through the example of the purification of therapeutically effective recombinant Bet v 1 (rBet v 1). All chromatography materials are commercially available from Amersham Biosciences (Freiburg, Germany).

EXAMPLE 1

Preparation of Hypoallergenic rBet v 1

Firstly, an *E. coli* lysate containing soluble rBet v 1 allergen is prepared by standard methods (Breiteneder H., et al., EMBO J. 1989, 8: 1935-8; Hoffmann-Sommergruber et al., Protein Exp. Purif. 9 (1), 1997: 33-39).

In order to remove nucleic acids, hydrophobic interaction chromatography is then carried out using phenyl-Sepharose in a Tris/ammonium sulfate buffer (20 mM Tris/HCl, 1 M ammonium sulfate, pH 8.0). The elution is carried out with distilled water. In preparation for the further purification steps to be carried out with weakly alkaline eluents, the residual ammonium sulfate is replaced by 20 mM NaCl by means of gel filtration through Sephadex G-25.

The protein solution pre-purified in this way is employed for anion exchange chromatography using Source 15Q, where the support material is equilibrated with an alkaline solution (20 mM NaOH, 11 mM $NaHCO_3$ and 20 mM NaCl). The relatively high pH of the starting solution causes virtually all target proteins to bind to the anion exchanger. The subsequent elution is carried out with increasing NaCl gradient (from 20 mM NaOH; 11 mM $NaHCO_3$; 20 mM NaCl to 20 mM NaOH; 11 mM $NaHCO_3$; 0.5 M NaCl) and causes removal of impurities (host-cell proteins) and active-ingredient fragments.

The next chromatography step is hydrophobic interaction chromatography by means of Source PHE. To this end, the eluate from the ion exchange chromatography is adjusted to 3 M NaCl, 20 mM NaOH, 11 mM $NaHCO_3$ by addition of corresponding amounts of a 5 M NaCl stock solution, a 2 M NaOH stock solution and sodium hydrogencarbonate. Under these conditions, rBet v 1 binds to the column material. The elution of the bound target protein is carried out using 20 mM NaOH.

As the final step, gel filtration is carried out through Superdex 75 under alkaline conditions. The chromatography solution is selected in such a way that neutralisation of the base added to the eluent results in the desired final formulation: 10 mM NaOH, 11 mM $NaHCO_3$ and 148.4 mM NaCl, which corresponds to the concentrations of physiological saline solution. The eluate from the gel filtration is finally neutralised using the acid HCl corresponding to the base NaOH used, resulting in a neutral pH and at the same time achieving the desired salt content of physiological saline solution. This is achieved through addition of 1/10 (v/v) 100 mM HCl.

EXAMPLE 2

Characterisation by SDS-PAGE

For characterisation of hypoallergenic rBet v 1 from Example 1, an SDS-PAGE (15%) is carried out. As can be seen from FIG. 1A, the natural nBet v 1 (track 2), recombinant rBet v 1 purified in a conventional manner by the method of Hoffmann-Sommergruber et al. (Protein Exp. Purif. 9 (1), 1997: 33-39) (track 4) and rBet v 1 purified in accordance with the invention (track 3) have the same molecular weight in the SDS-PAGE.

EXAMPLE 3

Determination of the IgE Activity Using a Serum Pool

In order to determine the IgE activity, the SDS-PAGE from Example 2 is blotted on nitrocellulose. After a blood serum pool from birch pollen allergy sufferers has been added to the blot, the blot is incubated with a conjugate consisting of an anti-IgE antibody and alkaline phosphatase. The colour reaction promoted by the alkaline phosphatase (FIG. 1B) shows an IgE activity of natural nBet v 1 and of recombinant, conventionally purified rBet v 1, but not of rBet v 1-MF purified in accordance with the invention.

EXAMPLE 4

Determination of the IgE Activity Using Individual Sera

In order to determine the IgE activity using blood sera from individual birch pollen allergy sufferers, nBet v 1 (position 3), recombinant, conventionally purified rBet v 1 (position 5) and rBet v 1 purified in accordance with the invention (position 4) are applied, as shown in FIG. 2A, to a nitrocellulose membrane and analysed analogously to Example 3, FIG. 2A shows that, with the exception of serum 5, where rBet v 1 purified in accordance with the invention has weak IgE activity, only natural nBet v 1 and recombinant, conventionally purified rBet v 1, but not rBet v 1 purified in accordance with the invention have IgE activity.

In order to determine the identity of the allergens investigated, the nitrocellulose membrane was incubated with various polygonal rabbit anti-Bet v 1 antibodies (samples 21 to 26) and with monoclonal mouse anti-Bet v 1 antibody 6B6 (sample 27) and subsequently treated analogously to Example 3 (FIG. 2B).

EXAMPLE 5

Quantification of IgE Binding

In an EAST inhibition assay carried out by the method of Suck et al. (Int. Arch. Allergy Immunol. 2000; 121: 284-291) using an allergy-sufferer serum pool, natural nBet v 1, recombinant, conventionally purified rBet v 1 and rBet v 1 purified in accordance with the invention are compared with one another with respect to the strength of their IgE binding (FIG. 3). It is found that rBet v 1 purified in accordance with the invention is reduced in IgE activity by more than 100 times compared with the other Bet v 1 proteins.

EXAMPLE 6

Determination of T-cell Stimulation

In order to determine the influence of the rBet v 1 allergen according to the invention on the growth of T-cells, a proliferation assay with T-cell lines (TCLs) and T-cell clones (TCCs) is carried out by the method of Schramm et al. (1999, J. Immunol. 162 (4): 2406-2414) (FIG. 4). It can be seen from a comparison of the stimulation indices (SI) that the T-cells of the investigated donors react at least as strongly with rBet v 1 as with natural nBet v 1 or conventional purified recombinant rBet v 1. Depending on the conditions selected, the reaction with rBet v 1 even exceeds the reaction with nBet v 1 or rBet v 1 by up to one third.

We claim:

1. A process for the preparation of a monomeric, full-length hypoallergenic major birch pollen allergen rBet v 1 comprising chromatographic purification of a monomeric, full-length soluble rBet v 1 crude protein, said purification comprising employing an essentially unbuffered aqueous NaOH base in a concentration range from 5 mM to 40 mM as eluent;

optionally adding $NaHCO_3$ and NaCl and subsequent neutralisation, wherein said monomeric, full-length soluble rBet v 1 crude protein is prepared by recombinant methods and the chromatographic purification comprises a sequential (a) first gel filtration; (b) anion exchange chromatography; (c) hydrophobic interaction chromatography; and (d) second gel filtration.

2. The process according to claim 1, wherein the monomeric, full-length soluble rBet v 1 crude protein prepared by recombinant methods is expressed in *Escherichia coli.*

3. The process according to claim 1, wherein the concentrations of NaOH, NaCl and $NaHCO_3$ in the eluent are each independently selected to allow setting of a physiological saline solution in the neutralisation step.

4. The process according to claim 1, comprising pre-purification of the monomeric, full-length rBet v 1 crude protein in a buffered solution by chromatography or by salt precipitation.

* * * * *